United States Patent [19]

Law

[11] Patent Number: 4,585,895

[45] Date of Patent: Apr. 29, 1986

[54] PROCESSES FOR THE PREPARATION OF MIXED SQUARAINE COMPOSITIONS

[75] Inventor: Kock-Yee Law, Fairport, N.Y.

[73] Assignee: Xerox Corporation, Stamford, Conn.

[21] Appl. No.: 703,569

[22] Filed: Feb. 20, 1985

[51] Int. Cl.[4] .......................... C07C 85/00; C07C 85/02; C07C 85/06

[52] U.S. Cl. .......................... 564/307

[58] Field of Search .......................... 564/307

[56] References Cited

U.S. PATENT DOCUMENTS

| | | | |
|---|---|---|---|
| 2,957,918 | 10/1960 | Smutny et al. | 260/590 |
| 3,617,270 | 11/1971 | Kampfer | 96/1.7 |
| 4,028,418 | 6/1977 | van den Brink et al. | 260/586 C |
| 4,052,209 | 10/1977 | Huffman et al. | 96/1.5 R |
| 4,159,387 | 6/1979 | Bellus | 560/185 |
| 4,216,172 | 8/1980 | Heine et al. | 568/364 |
| 4,222,902 | 9/1980 | Huffman et al. | 252/500 |
| 4,391,889 | 7/1983 | Mabuchi et al. | 430/59 |
| 4,396,694 | 8/1983 | Nagata et al. | 430/58 |
| 4,420,548 | 12/1983 | Sakai et al. | 430/59 |
| 4,471,041 | 9/1984 | Baranyi et al. | 430/59 |
| 4,486,520 | 12/1984 | Yanus | 430/59 |
| 4,489,148 | 12/1984 | Horgan | 430/59 |
| 4,490,452 | 12/1984 | Champ et al. | 430/58 |
| 4,500,621 | 2/1985 | Wurster | 430/72 |

OTHER PUBLICATIONS

"The Chemistry of Squaraines", Schmidt, Arthur H., Oxocarbon (1980) pp. 185-231, Edited: Robert West, Academic: New York Press.

*Primary Examiner*—Paul F. Shaver
*Attorney, Agent, or Firm*—E. O. Palazzo

[57] ABSTRACT

Disclosed is an improved process for the preparation of mixed squaraine compositions which comprises reacting a dialkyl squarate, a dialkyl aniline, and a dialkylhaloaniline in the presence of an aliphatic alcohol and an acid catalyst.

29 Claims, No Drawings

PROCESSES FOR THE PREPARATION OF MIXED SQUARAINE COMPOSITIONS

BACKGROUND OF THE INVENTION

This invention generally relates to an improved process for preparing squaraine compositions, and more specifically, the present invention is directed to an improved process for the preparation of mixed squaraine compositions of matter. In one embodiment, the present invention involves the preparation of certain mixed compositions by the reaction of a dialkyl squarate with dialkylaniline derivatives, and dialkylhaloanilines. The mixed squaraine compositions resulting from this process are useful for incorporation into layered photoresponsive imaging devices wherein, for example, the sensitivity thereof can be varied or enhanced, enabling these devices to be capable of being responsive to visible light, and infrared illumination needed for laser printing, where for example gallium arsenide diode lasers are selected. Accordingly, there is envisioned photoresponsive imaging members containing the mixed squaraine compositions prepared in accordance with the process of the present invention, situated between a photogenerating layer and a hole transport layer, or situated between a photogenerating layer and a supporting substrate of the member. The mixed squaraine compositions prepared in accordance with the process of the present invention also possess high charge acceptance, and low dark decay values, as well as excellent photosensitivity.

Layered photoresponsive imaging members with photogenerating layers and transport layers are known, reference U.S. Pat. No. 4,265,990. Examples of photogenerating layers disclosed in this patent include trigonal selenium, and phthalocyanines, while examples of transport layers that may be selected are comprised of certain diamine dispersed in an inactive resinous binder composition. Photoconductive imaging members with certain squaraine compositions, particularly hydroxy squaraines, are also known. There is thus disclosed in U.S. Pat. No. 4,415,639 the use of certain squaraine pigments, inclusive of hydroxy squaraines, in photoresponsive imaging devices. Specifically, there is described in this patent, the disclosure of which is totally incorporated herein by reference, an improved photoresponsive device comprised of a substrate, a hole blocking layer, an optional adhesive interface layer, an inorganic photogenerating layer, a hydroxy squaraine photoconductive composition capable of enhancing or reducing the intrinsic properties of the photogenerating layer, and a hole transport layer. Additionally, there is disclosed in U.S. Pat. No. 3,824,099 certain photosensitive hydroxy squaraine compositions. According to the disclosure of this patent, the squaraine compositions are photosensitive in normal electrostatographic imaging systems.

Additionally, in U.S. Pat. No. 4,471,041, there is illustrated squaraine compositions of matter, such as bis-9-(8-hydroxyjulolidinyl)squaraine, and the use of these compositions as imaging members. One of the imaging members disclosed is comprised of a supporting substrate, a hole blocking layer, an optional adhesive interface layer, an inorganic photogenerating layer, and a squaraine photoconducting composition layer capable of enhancing or reducing the intrinsic properties of the photogenerating layer.

Processes for preparing squaraine compositions generally involve the reaction of squaric acid with an amine. Thus, for example, the novel julolidinyl squaraine compositions disclosed in the referenced U.S. Pat. No. 4,471,041 patent are prepared by the reaction of an aromatic amine and squaric acid, in a molar ratio of from about 1.5:1 to 3:1, in the presence of a mixture of an aliphatic alcohol and an optional azeotropic cosolvent. About 200 milliliters of alcohol per 0.1 mole of squaric acid are used, while from about 40 milliliters to about 4,000 milliliters of azeotropic material are selected. The squaric acid reaction is generally accomplished at a temperature of from about 50 degrees Centigrade to about 130 degrees Centigrade. Illustrative examples of amine reactants include 8-hydroxyjulolidinyl, while examples of aliphatic alcohol selected include 1-butanol, with the azeotropic materials being aromatic compositions such as benzene and toluene. Moreover, there is disclosed in a copending application, U.S. Ser. No. 557,796/83, now U.S. Pat. No. 4,525,592, entitled Synthesis of Photoconductive Squaraines, the disclosure of which is totally incorporated herein by reference, processes for preparing squaraine compositions by the reaction of a dialkyl squarate and an aromtic aniline. More specifically, there is disclosed in this copending application an improved process for the preparation of squaraine compositions which comprises reacting a dialkyl squarate with an aniline in the presence of an acid cataylst and an aliphatic alcohol, at a temperature of from about 60 degrees Centigrade to about 160 degrees Centigrade.

There is also disclosed in a copending application U.S. Ser. No. 570,563, now U.S. Pat. No. 4,524,218, entitled Process For The Preparation Of Squaraine Compositions, the disclosure of which is totally incorporated herein by reference, a process for the preparation of photoconductive squaraines wherein the known squaric acid reaction is accomplished in the presence of a phenol, or a phenol squaraine. Further, there is disclosed in copending application U.S. Ser. No. 557,795, now U.S. Pat. No. 4,521,621, the disclosure of which is totally incorporated herein by reference, a process for obtaining novel unsymmetrical squaraine compositions from squaric acid, wherein there is formed a mixture of squaric acid, a primary alcohol, a first tertiary amine, and a second tertiary amine.

In another copending application, U.S. Ser. No. 06,038/84, entitled Processes For The Preparation Of Mixed Squaraine Compositions, there is described the reaction of squaric acid, an aromatic amine, and a fluoroaniline. The disclosure of this copending application is totally incorporated herein by reference.

While the above processes for preparing squaraine compositions may be suitable for their intended purposes, there continues to be a need for other processes wherein mixed squaraine compositions, useful as photoconductive materials, can be prepared. Additionally, there remains a need for simple, economical processes for preparing mixed squaraine compositions wherein the squaraine products obtained contain substantially less impurities than those squaraines resulting from the squaric acid process, as it is believed that the presence of impurities in the squaraine compositions resulting from the squaric acid process causes the photosensitivity of these compositions to vary significantly, and in many instances, to be lower than the squaraine compositions prepared in accordance with the process of the present invention. Further, there continues to be a need for mixed squaraine compositions which, when selected for layered photoresponsive imaging devices, allow the generation of acceptable images, and wherein such devices can be repeatedly used in a number of imaging cycles without deterioration thereof from the machine environment or surrounding conditions. Moreover, there remains a need for processes for preparing certain mixed squaraine compositions, wherein the resulting products when incorporated into imaging members exhibit excellent dark decay and superior photosensitivity. Also, there is provided in accordance with the process of the present invention xerographic photoconductive imaging members comprised of mixed squaraine photogenerating materials possessing desirable sensitivity, low dark decay, high charge acceptance values, and desirable dispersion particle sizes.

SUMMARY OF THE INVENTION

It is therefore an object of the present invention to provide improved processes for preparing mixed squaraine compositions.

In another object of the present invention, there are provided improved processes for preparing certain mixed squaraine compositions, with enhanced photosensitivity, excellent dark decay properties, and acceptable charge acceptance.

In yet another object of the present invention, there are provided simple, economical processes for preparing certain mixed squaraine compositions.

In still a further object of the present invention, there are provided improved processes for obtaining mixed squaraine compositions of matter, which contain substantially less impurities than similar squaraines prepared by the known squaric acid process.

In another object of the present invention, there are provided improved process for obtaining mixed squaraines, by the reaction of a dialkyl squarate with a dialkylaniline, and a dialkylhaloaniline.

A further object of the present invention resides in the preparation of mixed squaraine compositions wherein the particle sizes of the resulting products are desirably less than about two microns or about a factor of two smaller in many instances than those squaraines prepared from the known squaric acid process.

These and other objects of the present invention are generally accomplished by the reaction of a dialkyl squarate, a dialkylaniline, and a dialkylhaloaniline in the presence of an aliphatic alcohol, and a catalyst. More specifically, the process of the present invention comprises reacting at an effective temperature, for example, from about 60 degrees Centigrade to about 160 degrees Centigrade, a dialkylsquarate, a dialkyl aniline, and a dialkylfluoroaniline in the presence of an acid catalyst, and an aliphatic alcohol. The reactions involved are represented by the following illustrative equations:

I. General Reaction

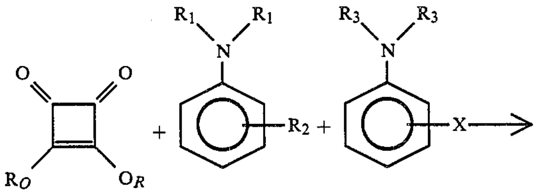

-continued

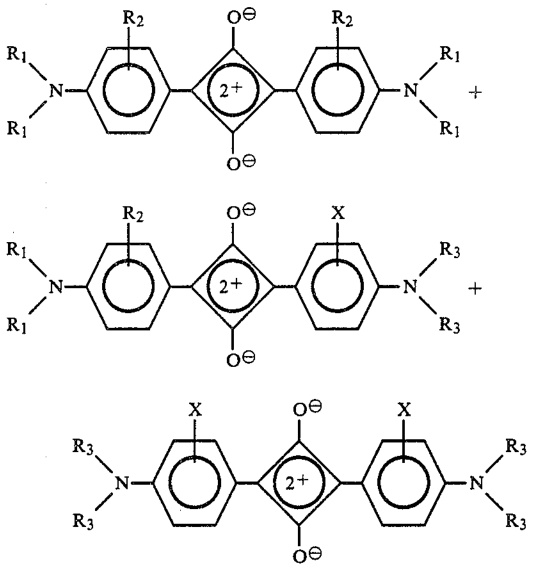

II. Specific Reaction

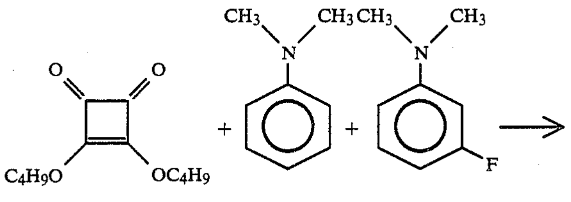

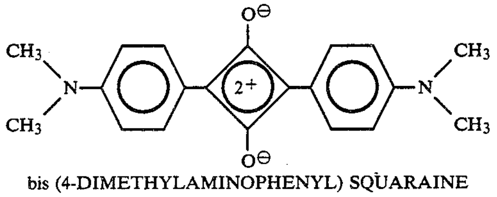

bis (4-DIMETHYLAMINOPHENYL) SQUARAINE

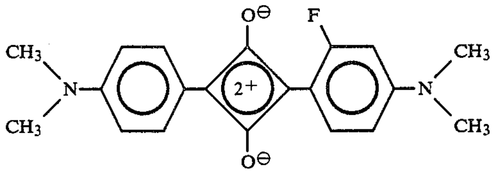

2-FLUORO-4-DIMETHYLAMINOPHENYL-4'-DIMETHYLAMINOPHENYL-SQUARAINE

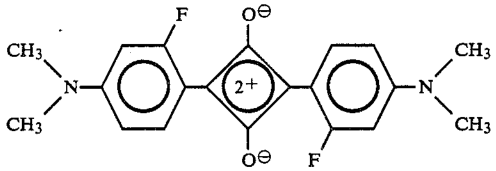

bis (2-FLUORO-4-DIMETHYLAMINOPHENYL) SQUARAINE wherein R, $R_1$, and $R_3$ are independently selected from the group consisting of alkyl, $R_2$ is independently selected from the group consisting of alkyl, alkoxy, and hydroxy, and X is a halogen atom inclusive of fluorine, chlorine, or bromine.

Alkyl substituents include those containing from about 1 carbon atom to about 10 carbon atoms, and preferably from 1 carbon atom to about 6 carbon atoms, such as methyl, ethyl, propyl, butyl, pentyl, hexyl, and the like. Preferred alkyl groups are methyl, ethyl, propyl, and butyl. Examples of alkoxy substituents are those with from about 1 to 10 carbon atoms, inclusive of methoxy, propoxy, ethoxy, butoxy, pentoxy, and the like.

Illustrative examples of dialkyl squarate reactants include dimethyl squarate, dipropyl squarate, diethyl squarate, dibutyl swuarate, dipentyl squarate, dihexyl squarate, diheptyl squarate, dioctyl squarate, and the like, with the dimethyl, diethyl, dipropyl, and dibutyl squarates being preferred. Illustrative examples of aniline reactants are N,N-dimethylaniline, N,N-diethylaniline, N,N-dipropylaniline, N,N-dibutylaniline, N,N-dipentylaniline, N,N-dihexylaniline, 3-methyl-N,N-dimethylaniline, 3-hydroxy-N,N-dimethylaniline, 3-hydroxy-N,N-diethylaniline, 3-ethyl-N,N-dimethylaniline, 3-methoxy-N,N-dimethylaniline, and the like. Examples of dialkylhaloaniline reactants include 3-fluoro-N,N-dimethylaniline, 2-fluoro-N,N-dimethylaniline, 3-chloro-N,N-dimethylaniline, 2-chloro-N,N-dimethylaniline, and other similar haloaniline compounds.

The reaction is preferably accomplished in the presence of an acid catalyst, examples of which include various inorganic acids, and organic acids, such as sulfuric acid, trichloroacetic acid, oxalic acid, toluene sulfonic acid, and the like, with sulfuric acid and trichloroacetic being preferred. Also known solvents, such as aliphatic alcohols, including methanol, ethanol, propanol, butanol, amyl alcohol, and the like are selected for the purpose of forming a solution of the squarate and the acid catalyst. Other solvents can be used providing the objectives of the present invention are accomplished.

Reaction temperatures can vary over a wide range, and are generally dependent on the reactants selected, and other similar factors. Generally, the reaction temperature is established at a temperature at which the aliphatic alcohol boils. Thus, for example, the reaction temperature is generally from about 60 degrees Centigrade to about 160 degrees Centigrade, and is preferably from about 98 degrees Centigrade to about 140 degrees Centigrade, especially when the aliphatic alcohol selected is of a carbon chain length of from about 3 carbon atoms to about 5 carbon atoms.

The amount of dialkyl squarate, dialkylaniline, dialkylhaloaniline, alcohol, and catalyst selected depend on a number of factors, including the specific reactants used, and the reaction temperature involved. Generally, however, from about 5 millimoles, to about 50 millimoles, of dialkyl squarate, with about 3 millimoles to about 100 millimoles of aniline, from about 7 millimoles to about 100 millimoles of dialkylhaloaniline, and from about 5 milliliters to about 200 milliliters of aliphatic alcohol are selected. Also, from about 4 millimoles to about 40 millimoles of protons, are contained in the optional acid catalyst.

Mixed squaraine products resulting subsequent to separation from the reaction mixture, by known techniques including filtration, were identified primarily by elemental analysis, and proton NMR spectroscopy.

Illustrative examples of specific mixed squaraine compositions resulting from the process of the present invention include bis(4-dimethylaminophenyl) squaraine, 83 to 84 mole percent, 2-fluoro-4-dimethylaminophenyl-4'-dimethylaminophenyl squaraine, 15 to 16 mole percent, and bis(2-fluoro-4-dimethylaminophenyl) squaraine 1 to 2 mole percent; bis(4-dimethylaminophenyl) squaraine, 59 mole percent, 2-fluoro-4-dimethylaminophenyl-4'-dimethylaminophenyl squaraine, 35 mole percent, and bis(2-fluoro-4-dimethylaminophenyl) squaraine, 6 mole percent; bis(4-dimethylaminophenyl) squaraine, 14 mole percent, 2-fluoro-4-dimethylaminophenyl-4'-dimethylaminophenyl squaraine, 42 mole percent, and bis(2-fluoro-4-dimethylaminophenyl) squaraine, 44 mole percent; bis(4-dimethylaminophenyl) squaraine, 95 to 99 mole percent, and 3-fluoro-4-dimethylaminophenyl 4'-dimethylaminophenyl squaraine, 1 to 5 mole percent; bis(4-dimethylaminophenyl) squaraine, 81 mole percent, and 2-chloro-4-dimethylaminophenyl-4'-dimethylaminophenyl squaraine, 19 mole percent.

In one specific embodiment, the process of the present invention comprises forming a solution of the dialkyl squarate reactant, and acid catalyst, by mixing together from about 5 to about 50 millimoles of a dialkyl squarate, with from about 0.1 milliliters to about 1 milliliter of sulfuric acid, and from about 5 milliliters to about 200 milliliters of aliphatic alcohol. This mixture is then heated to a temperature of from about 60 degrees Centigrade to about 160 degrees Centigrade, with continual stirring. Thereafter there is added to the reaction mixture an aniline mixture of from about 2.5 millimoles of N,N-dimethylaniline and about 7.5 millimoles of 3-fluoro-N,N-dimethylaniline, to about 40 millimoles of N,N-dimethylaniline and 75 millimoles of 3-fluoro-N,N-dimethylaniline. After heating, for a period of from about 24 to about 40 hours, the reaction mixture is allowed to cool and there is isolated by filtration the desired squaraine product. The mixed products obtained were of a small particle size, ranging from about less than 0.1 microns to about less than 2.0 microns, which small particle sizes provide for the superior dispersion of these squaraine compositions in a resinous binder composition, thereby enabling excellent dark decay properties, high charge acceptance and superior photosensitivity for photoconductive members thereof, as compared to devices containing similar squaraine compositions prepared by the squaric acid process.

Mixed squaraine compositions prepared in accordance with the process of the present invention are useful in photoconductive imaging members. Thus, there can be prepared a layered photoresponsive imaging member comprised of a supporting substrate, a hole transport layer, and a photoconductive layer comprised of the mixed squaraine compositions prepared in accordance with the process of the present invention, which composition is situated between the supporting substrate and a hole transport layer. In another embodiment, the photoresponsive device envisioned is comprised of a substrate, a photoconducting layer, comprised of the mixed squaraine compositions prepared in accordance with the process of the present invention, and situated between the photoconducting squaraine layer, and the supporting substrate, a hole transport layer. Additionally, there can be prepared photoresponsive imaging members useful in printing processes wherein the imaging member is comprised of a layer of the squaraine photoconductive composition prepared in accordance with the process of the present invention, situated between a photogenerating layer and a hole transport layer; or wherein the squaraine photoconductive squaraine composition layer is situated between a photogenerating layer, and the supporting substrate of such a device. In the latter devices, the photoconductive layer comprised of the mixed squaraine compositions serves to enhance or reduce the intrinsic properties of the photogenerating layer in the infrared and/or visible range of the spectrum. These and other imaging members are illustrated in U.S. Pat. No. 4,471,041, entitled Photoconductive Devices Containing Novel Squaraine Compositions, the disclosure of which is totally incorporated herein by reference.

One specific improved photoresponsive imaging member containing therein the mixed squaraines prepared in accordance with the process of the present invention is comprised in the order stated of (1) a supporting substrate, (2) a hole blocking layer, (3) an optional adhesive interface layer, (4) an inorganic photogenerator layer, (5) a photoconductive layer comprised of the mixed squaraine compositions, and (6) a hole transport layer. A second specific photoresponsive imaging member is comprised of (1) a supporting substrate, (2) a photoconductive layer comprised of the mixed squaraine compositions prepared in accordance with the process of the present invention, and (3) an arylamine hole transport layer.

The photoresponsive imaging members described can be prepared by a number of known methods, reference for example the copending applications, and U.S. patents described hereinbefore, the process parameters and the order of coating of the layers being dependent on the imaging members desired. Thus, for example, a three layered photoresponsive imaging member can be prepared by vacuum sublimation of the photoconducting layer on a supporting substrate, and subsequently depositing by coating a solution of the hole transport layer. In another process variant, the layered photoresponsive imaging members can be prepared by providing the conductive substrate containing a hole blocking layer and an optional adhesive layer, and applying thereto by solvent coating processes, laminating processes, or other methods, a photogenerating layer, a photoconductive composition comprised of the mixed squaraines prepared in accordance with the process of the present invention and a hole transport layer.

Also, the improved photoresponsive imaging members of the present invention can be incorporated into various imaging systems, such as those conventionally known as xerographic imaging processes. Additionally, the improved photoresponsive imaging members of the present invention with an inorganic photogenerating layer, and a photoconductive layer comprised of the mixed squaraines prepared in accordance with the process of the present invention can function simultaneously in imaging and printing systems with visible light and/or infrared light. In this embodiment, the improved photoresponsive imaging members of the present invention may be negatively charged, exposed to light in a wavelength of from about 400 to about 1,000 nanometers, either sequentially or simultaneously, followed by developing the resulting image and transferring to paper. The above sequence may be repeated many times.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

Dibutyl squarate, 1.13 grams, 5 millimoles, was placed in 5 milliliters of water saturated 1-butanol, containing 0.1 milliliters of concentrated sulfuric acid in a 100 milliliter 3-neck flask equipped with a magnetic stir bar, and a nitrogen inlet. The resulting reaction mixture was then stirred and caused to reflux by heating an oil bath surrounding the flask, to a temperature of about 120 to 130 degrees Centigrade. Subsequently, there was added over a period of about 8 hours, about 2 drops every 30 minutes, a mixture of 0.31 grams of N,N-dimethylaniline, and 1.08 grams of 3-fluoro-N,N-dimethylaniline. On completion of the addition the color of the reaction mixture was light yellow green. Refluxing was continued for about 40 hours. After cooling the mixture to room temperature, the precipitated product was separated therefrom by filtration with a fine sintered glass funnel, followed by washing with methanol until the filtrate was light blue in color. There resulted 0.52 grams of a mixture of bis(4-dimethylaminophenyl) squaraine, 14 mole percent, 2-fluoro-4-dimethylaminophenyl-4'-dimethylaminophenyl squaraine, 42 mole percent, and bis-(2-fluoro-4-dimethylaminophenyl) squaraine, 44 mole percent. The fluorine content of the product mixture was 6.3 percent as determined by elemental analysis. Also, the molar concentration, mole percent, of each component in the product mixture was determined by proton NMR analysis.

EXAMPLE II

The process of Example I was repeated with the exception that 0.62 grams of N,N-dimethylaniline, and 0.71 grams of 3-fluoro-N,N-dimethylaniline were selected. There resulted 0.58 grams of a mixture of bis(4-dimethylaminophenyl) squaraine, 59 mole percent, 2-fluoro-4-dimethylaminophenyl-4'-dimethylaminophenyl squaraine, 35 mole percent, and bis(2-fluoro-4-dimethylaminophenyl) squaraine, 5 mole percent. The fluorine content of the mixture was 2.75 percent as determined by elemental analysis.

EXAMPLE III

The process of Example 1 was repeated with the exception that 0.86 grams of N,N-dimethylaniline, and 0.43 grams of 3-fluoro-N,N-dimethylaniline were selected. There resulted 0.70 grams of a mixture of bis(4-dimethylaminophenyl) squaraine, 83 to 84 mole percent, 2-fluoro-4-dimethylaminophenyl-4'-dimethylaminophenyl squaraine, 16 mole percent, and bis(2-fluoro-4-dimethylaminophenyl) squaraine, 1 to 2 mole percent. The fluorine content of the mixture was 1.08 percent as determined by elemental analysis.

EXAMPLE IV

The process of Example I was repeated with the exception that 0.31 grams of N,N-dimethylaniline, and 1.08 grams of 2-fluoro-N,N-dimethylaniline were selected. There resulted 0.09 grams of a mixture of bis(4-dimethylaminophenyl) squaraine, 95 to 99 mole percent, and 3-fluoro-4-dimethylaminophenyl-4'-dimethylaminophenyl squaraine, 1 to 5 percent. Th fluorine content of the mixture was 0.45 percent as determined by elemental analysis.

EXAMPLE V

The process of Example I was repeated with the exception that 0.31 grams of N,N-dimethylaniline, and 1.19 grams of 3-chloro-N,N-dimethylaniline were selected. There resulted 0.11 grams of a mixture of bis(4-dimethylaminophenyl) squaraine, 81 mole percent, and 2-chloro-4-dimethylaminophenyl-4'-dimethylaminophenyl squaraine, 19 mole percent. The chlorine content of the mixture was 1.6 percent as determined by elemental analysis.

Although the invention has been described with reference to specific preferred embodiments, it is not intended to be limited thereto, rather those skilled in the art will recognize that variations and modifications may be made therein which are within the spirit of the present invention and within the scope of the following claims.

What is claimed is:

1. An improved process for the preparation of mixed squaraine compositions which comprises reacting a dialkyl squarate, a dialkyl aniline, and a dialkylhaloaniline in the presence of an aliphatic alcohol and an acid catalyst.

2. A process in accordance with claim 1 wherein the reaction is accomplished at a temperature of from about 60 degrees Centigrade to about 160 degrees Centigrade.

3. A process in accordance with claim 1 wherein the dialkyl squarate is selected from the group consisting of a dimethyl squarate, diethyl squarate, dipropyl squarate, dibutyl squarate, dipentyl squarate, dihexyl squarate and diheptyl squarate.

4. A process in accordance with claim 1 wherein the dialkyl squarate is dimethyl squarate.

5. A process in accordance with claim 1 wherein the dialkylhaloaniline is selected from the group consisting of 3-fluoro-N,N-dimethylaniline, 2-fluoro-N,N-dimethylaniline, and 3-chloro-N,N-dimethylaniline.

6. A process in accordance with claim 1 wherein the aliphatic alcohol is 1-butanol, 1-propanol, or amyl alcohol.

7. A process in accordance with claim 1 wherein the resulting mixed squaraine composition is comprised of I, bis(4-dimethylaminophenyl) squaraine, II, 2-fluoro-4-dimethylaminophenyl-4'-dimethylaminophenyl squaraine, and III, bis(2-fluoro-4-dimethylaminophenyl) squaraine.

8. A process in accordance with claim 7 wherein the mixture contains about 84 mole percent of I, about 15 to 16 mole percent of II, and about 1 to 2 mole percent of III.

9. A process in accordance with claim 7 wherein the mixture contains about 59 mole percent of I, about 35 mole percent of II, and about 6 mole percent of III.

10. A process in accordance with claim 7 wherein the mixture contains about 14 mole percent of I, about 42 mole percent of II, and about 44 mole percent of III.

11. A process in accordance with claim 1 wherein the resulting mixed squaraine composition is comprised of IV, bis(4-dimethylaminophenyl) squaraine, and V, 3-fluoro-4-dimethylaminophenyl-4'-dimethylaminophenyl squaraine.

12. A process in accordance with claim 11 wherein the mixture contains about 95 to 99 mole percent of IV, and about 1 to 5 mole percent of V.

13. A process in accordance with claim 1 wherein the resulting mixed squaraine product is comprised of VI, bis(4-dimethylaminophenyl) squaraine, and VII, 2-chloro-4-dimethylaminophenyl-4'-dimethylaminophenyl squaraine.

14. A process in accordance with claim 13, wherein the mixture contains about 81 mole percent of VI, and about 19 mole percent of VII.

15. A process in accordance with claim 1 wherein the reaction temperature is from about 98 degrees Centigrade to about 140 degrees Centigrade.

16. A process for the preparation of the mixed squaraine compositions

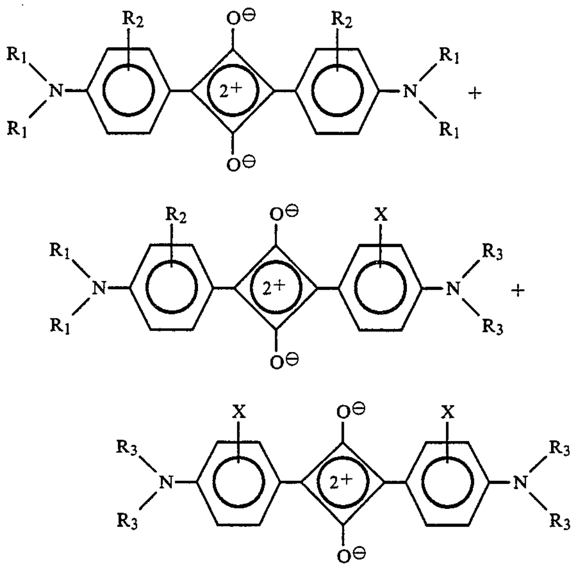

which comprises reacting in the presence of an optional acid catalyst and an aliphatic alcohol an alkyl squarate of the following formula with a dialkylaniline, and dialkylhaloaniline of the following formulas:

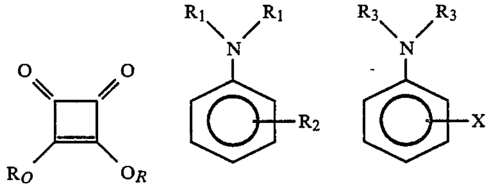

wherein R, $R_1$, $R_3$, are independently selected from the group consisting of alkyl, and $R_2$ is independently selected from the group consisting of alkyl, alkoxy, and hydroxy, and x is a halogen.

17. A process in accordance with claim 16 wherein R, $R_1$, and $R_3$, are alkyl groups of from about 1 carbon atom to about 10 carbon atoms.

18. A process in accordance with claim 16 the alkyl substituents are methyl.

19. A process in accordance with claim 16 wherein $R_2$ is an alkyl group of from 1 to about 10 carbon atoms.

20. A process in accordance with claim 16 wherein $R_2$ is an alkoxy group of from 1 to about 10 carbon atoms.

21. A process in accordance with claim 16 wherein X is fluorine.

22. A process in accordance with claim 16 wherein X is chlorine.

23. A process in accordance with claim 1 wherein the dialkylaniline is selected from the group consisting of a N,N-dimethylaniline, N,N-diethylaniline, N,N-dipropylaniline, N,N-dibutylaniline, N,N-dipentylaniline, 3-fluoro-N,N-dimethylaniline, 3-hydroxy-N,N-dimethylaniline, 3-methyl-N,N-dimethylaniline, 3-hydroxy-N,N-diethylaniline, and 3-methoxy-N,N-dimethylaniline.

24. A process in accordance with claim 1 wherein the acid catalyst is selected from the group consisting of sulfuric acid, trichloroacetic acid, and oxalic acid.

25. An improved process for the preparation of a mixture of squaraine compositions consisting essentially of the reaction of a dialkyl squarate, a dialkyl aniline, and a dialkylhaloaniline in the presence of an aliphatic alcohol and an acid catalyst, which reaction is accomplished at a temperature of from about 60 degrees Centigrade to about 160 degrees Centigrade.

26. A process in accordance with claim 25 wherein the dialkyl squarate is selected from the group consisting of dimethyl squarate, diethyl squarate, dipropyl squarate, dibutyl squarate, dipentyl squarate, dihexyl squarate and diheptyl squarate.

27. A process in accordance with claim 25 wherein the resulting mixed squaraine composition is comprised of I, bis(4-dimethylaminophenyl) squaraine; II, 2-fluoro-4-dimethylaminophenyl-4'-dimethylaminophenyl squaraine; and III, bis(2-fluoro-4-dimethylaminophenyl) squaraine.

28. A process in accordance with claim 25 wherein the dialkylhaloaniline is selected from the group consisting of 3-fluoro-N,N-dimethylaniline, 2-fluoro-N,N-dimethylaniline, and 3-chloro-N,N-dimethylaniline.

29. A process in accordance with claim 25 wherein the dialkylaniline is selected from the group consisting of a N,N-dimethylaniline, N,N-diethylaniline, N,N-dipropylaniline, N,N-dibutylaniline, N,N-dipentylaniline, 3-fluoro-N,N-dimethylaniline, 3-hydroxy-N,N-dimethylaniline, 3-methyl-N,N-dimethylaniline, 3-hydroxy-N,N-diethylaniline, and 3-methoxy-N,N-dimethylaniline.

* * * * *